(12) United States Patent
Boecker et al.

(10) Patent No.: US 10,531,660 B2
(45) Date of Patent: Jan. 14, 2020

(54) SIMPLE AND INEXPENSIVE PRODUCTION OF A COMPOSITION COMPRISING INSECTICIDE-WAX PARTICLES

(71) Applicant: BAYER CROPSCIENCE AKTIENGESELLSCHAFT, Duesseldorf (DE)

(72) Inventors: Thomas Boecker, Leichlingen (DE); Volker Gutsmann, Langenfeld (DE); Jens Hepperle, Cologne (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/322,796

(22) PCT Filed: Jul. 1, 2015

(86) PCT No.: PCT/EP2015/064945
§ 371 (c)(1),
(2) Date: Dec. 29, 2016

(87) PCT Pub. No.: WO2016/001285
PCT Pub. Date: Jan. 7, 2016

(65) Prior Publication Data
US 2017/0164611 A1 Jun. 15, 2017

(30) Foreign Application Priority Data
Jul. 3, 2014 (EP) .................................... 14175523

(51) Int. Cl.
*A01N 53/00* (2006.01)
*A01N 25/08* (2006.01)
*A01N 25/04* (2006.01)
*A01N 25/26* (2006.01)

(52) U.S. Cl.
CPC ............. *A01N 25/26* (2013.01); *A01N 25/04* (2013.01); *A01N 25/08* (2013.01); *A01N 53/00* (2013.01)

(58) Field of Classification Search
None
See application file for complete search history.

(56) References Cited

U.S. PATENT DOCUMENTS

| 6,310,117 B1 * | 10/2001 | Sawada | C08J 3/124 427/222 |
|---|---|---|---|
| 9,451,764 B2 | 9/2016 | Gutsmann et al. | |
| 2005/0014646 A1 * | 1/2005 | Schwarz | A01N 25/32 504/111 |
| 2007/0145618 A1 * | 6/2007 | Finney | B01J 13/02 264/4.1 |
| 2012/0156273 A1 * | 6/2012 | Gutsmann | A01N 25/04 424/405 |

FOREIGN PATENT DOCUMENTS

| DE | 195 32 538 A1 | 3/1997 |
| WO | 2012080188 A1 | 6/2012 |
| WO | 2014020295 A1 | 2/2014 |
| WO | WO2014020295 | * 2/2014 |

OTHER PUBLICATIONS

International Search Report of PCT/EP2015/064945 dated Jul. 1, 2015.
European Search Report of EP 14 17 5523 dated Dec. 11, 2014.
Ullmann's Encyclopedia of Industrial Chemistry, vol. 39, pp. 111-172 (2012), published by Wiley-VCH Verlag GmbH & Co., Weinheim.

* cited by examiner

*Primary Examiner* — Abigail Vanhorn
(74) *Attorney, Agent, or Firm* — McBee Moore & Vanik IP, LLC

(57) ABSTRACT

The present invention relates to a simple and inexpensive production of a composition comprising insecticide-wax particles, which is used especially for long-lasting control of animal pests (arthropods) on various surfaces.

15 Claims, 1 Drawing Sheet

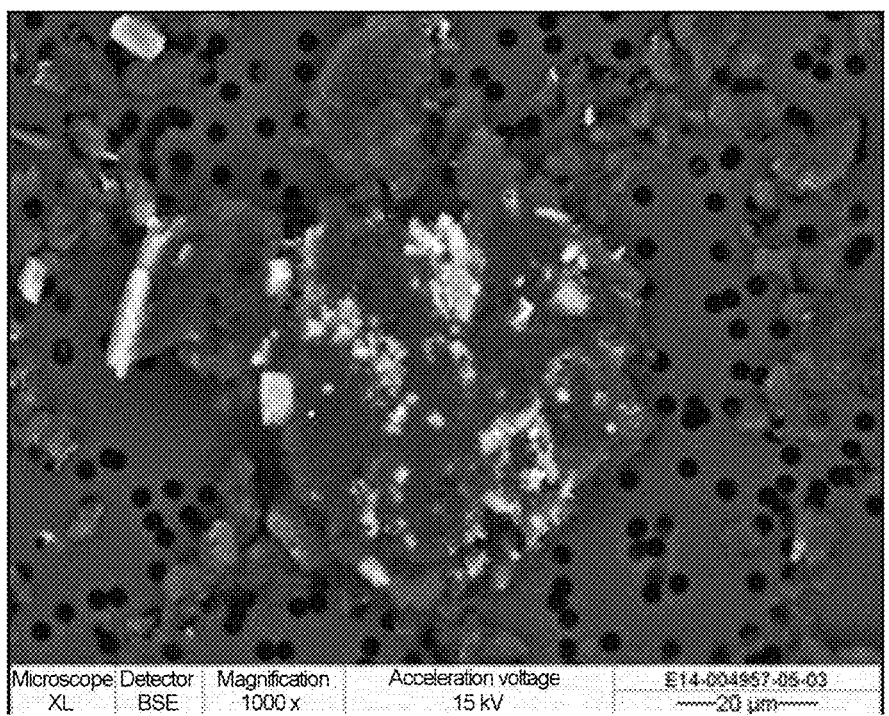

SIMPLE AND INEXPENSIVE PRODUCTION OF A COMPOSITION COMPRISING INSECTICIDE-WAX PARTICLES

CROSS REFERENCE TO RELATED APPLICATIONS

This application is a § 371 National Stage Application of PCT/EP2015/064945, filed Jul. 1, 2015, which claims priority to European Application No. 14175523.1 filed Jul. 3, 2014.

BACKGROUND OF THE INVENTION

Field of the Invention

The present invention relates to a simple and inexpensive production of a composition comprising insecticide-wax particles, which is used especially for long-lasting control of animal pests (arthropods) on various surfaces.

Description of Related Art

Compositions comprising insecticide-wax particles have already been described in detail in WO2012/080188 A1. This application shows how insecticide-wax particles can be produced via spray solidification and then used, for example, as a constituent of aqueous suspension concentrates or spray liquors produced therefrom, or else as ready-to-use (RTU) formulations. The insecticide-wax particles obtained by spray solidification have coarse grains, i.e. have a median particle size d50 of 5-40 µm, and are obtained by first producing a melt from the wax. Then the active ingredient is incorporated homogeneously into the melt, for example using a magnetic stirrer. The spray solution is then atomized from the reservoir into a controlled environment, for example with the aid of a pump via a nozzle having a suitably chosen diameter. The reservoir, the pump, the nozzle and all the conduits that come into contact with the spray solution are heated to at least 90° C. The spray solution is atomized at a spray gas pressure of about 0.8 bar into a much colder environment, for example into a spray tower. The rapid cooling on entry into the cold spray tower results in very rapid solidification of the spray droplets of the spray solution to obtain solid, approximately spherical particles. The atomizer nozzle is chosen such that the solid active ingredient-wax particles obtained have a particle size d50 of about 10 to 35 µm. The particles obtained are removed from the spray tower in a customary manner, for example with the aid of a cyclone. The active ingredient is distributed homogeneously within the particles. When the active ingredient-wax particles obtained are subsequently incorporated in accordance with the invention into an aqueous suspension, the active ingredient diffuses out of the interior of the particles to the surface (carrier/water interface) and crystallizes out there. Thus, when the particles are introduced into water, a phase conversion takes place from molecularly disperse or amorphous to crystalline, and migration of the active ingredient out of the particle interior and active ingredient enrichment at the surface takes place. It has been assumed that this specific structure of the particles according to the invention is the cause of the improved effect (rapid bioavailability and improved long-term biological effect).

The disadvantages of the use of spray solidification technology for production of the above-described composition comprising insecticide-wax particles are high capital costs for the apparatus needed for the production, difficulty of process control and, under some circumstances, a relatively low yield. The effect of these disadvantages is that the production costs of the compositions comprising insecticide-wax particles are high.

The problem addressed by the present invention was accordingly that of providing a much simpler and less expensive production process which can produce compositions which comprise insecticide-wax particles and have the same properties as those described in WO2012/080188 A1. The properties of the compositions comprising insecticide-wax particles described in WO2012/080188 A1 are rapid bioavailability and improved long-term biological effect. This is especially true in the case of treatment of porous and especially alkaline porous surfaces such as concrete, render, brick, wood (treated and untreated), ceramic, straw or thatch, or chalk-containing, lime-containing, gypsum-containing, cement-containing and loam-containing surfaces. At the same time, the effect in the case of use on nonporous surfaces remains essentially unaffected.

SUMMARY

It has now been found that, surprisingly, the insecticide-wax particles in the composition comprising insecticide-wax particles can also be produced by mixing wax with the active insecticidal ingredient (without adding water or further additives/auxiliaries) at elevated temperatures and dry grinding after the mixture has cooled down.

Thus, the problem is solved by a process for producing an insecticidal composition comprising at least one active insecticidal ingredient, wax having a melting point of 50 to 160° C. under standard conditions, water and standard additives and/or auxiliaries, wherein the insecticidal active ingredient(s) is/are dispersed in the wax and the insecticidal-containing wax is present in the composition in the form of particles, wherein the particles have a mean particle size of 5 to 40 µm, and crystals of the active ingredient(s) are present at the surface of the particles, comprising the following steps:
(a) melting wax and dispersing active insecticidal ingredient(s) in the melt without adding water and without adding additives and auxiliaries,
(b) cooling the mixture down in a vessel as a block and then comminuting the block by dry grinding,
(c) dispersing the resultant particles in water with addition of standard additives and auxiliaries.

BRIEF DESCRIPTION OF THE DRAWINGS

The FIGURE describes an embodiment as described herein.

DETAILED DESCRIPTION OF A PREFERRED EMBODIMENT

The prior art does not describe such a process. For example, WO2010/031508 A2 describes the production of wax dispersions with active agrochemical ingredients. In the production process described, however, it is absolutely necessary that the wax is dissolved in water or with the aid of surfactants while supplying heat. Only thereafter is the active agrochemical ingredient added. However, the present production process is characterized in that the active ingredient-wax particles are produced without adding water and without adding additives and auxiliaries. Advantages of the process according to the invention compared to those described in WO2010/031508 A2 include lower production costs and increased flexibility in the establishment of the desired particle size distribution.

Preferably, the compositions according to the invention comprise one or more active insecticidal ingredients which are selected from those which follow. The active ingredients specified in this description by their common name are known, for example, from "The Pesticide Manual" 14th ed., British Crop Protection Council 2006, and the website http://www.alanwood.net/pesticides.

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulphan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulphoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulphotep, tebupirimfos, temephos, terbufos, tetrachlorvinphos, thiometon, triazophos, triclorfon and vamidothion.

(2) GABA-gated chloride channel antagonists, for example organochlorines, for example chlordane and endosulphan (alpha-); or fiproles (phenylpyrazoles), for example ethiprole, fipronil, pyrafluprole and pyriprole.

(3) Sodium channel modulators/voltage-dependent sodium channel blockers, for example pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, fluvalinate (tau-), halfenprox, imiprothrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin and ZXI 8901; or DDT; or methoxychlor.

(4) Nicotinergic acetylcholine receptor agonists, for example neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), for example spinosyns, e.g. spinetoram and spinosad.

(6) Chloride channel activators, for example avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active compounds having unknown or nonspecific mechanisms of action, for example fumigants, for example methyl bromide and other alkyl halides; or chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Abl.

(12) Oxidative phosphorylation inhibitors, ATP disruptors, for example diafenthiuron; or organotin compounds, for example azocyclotin, cyhexatin, fenbutatin oxide; or propargite; tetradifon.

(13) Oxidative phosphorylation decouplers that disrupt the H proton gradient, for example, chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or rotenone (Derris).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(26) Ryanodine receptor effectors, for example diamides, for example chlorantraniliprole (Rynaxypyr), cyantraniliprole (Cyazypyr) and flubendiamide.

Further active ingredients with unknown mechanism of action, for example azadirachtin, amidoflumet, benzoximate, bifenazate, chinomethionat, cryolite, cyflumetofen, dicofol, flufenerim, pyridalyl and pyrifluquinazon; or the known active compounds below: 4-{[(6-bromopyrid-3-yl)methyl](2-fluoroethyl)amino}furan-2(5H)-one (known from WO 2007/115644), 4-{[(6-fluoropyrid-3-yl)methyl](2,2-difluoroethyl)amino}furan-2(5H)-one (known from WO 2007/115644), 4-{[(2-chloro-1,3-thiazol-5-yl)methyl](2- fluoroethyl)amino}furan-2(5H)-one (known from WO 2007/115644), 4-{[(6-chloropyrid-3-yl)methyl](2-fluoroethyl)amino}furan-2(5H)-one (known from WO 2007/115644), 4-{[(6-chloropyrid-3-yl)methyl](2,2-difluoroethyl)amino}furan-2(5H)-one (known from WO 2007/115644), 4-{[(6-chloro-5-fluoropyrid-3-yl)methyl](methyl)amino}furan-2(5H)-one (known from WO 2007/115643), 4-{[(5,6-dichloropyrid-3-yl)methyl](2-fluoroethyl)amino}furan-2(5H)-one (known from WO 2007/115646), 4-{[(6-chloro-5-fluoropyrid-3-yl)methyl](cyclopropyl)amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-$\lambda^4$-sulphanylidenecyanamide (known from WO 2007/149134), [1-(6-chloropyridin-3-yl)ethyl](methyl)oxido-$\lambda^4$-sulphanylidenecyanamide (known from WO 2007/149134) and its diastereomers (A) and (B)

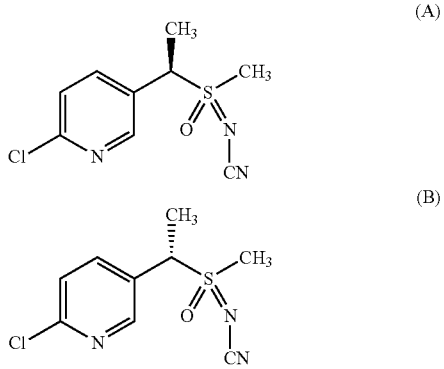

(likewise known from WO 2007/149134), [(6-trifluoromethylpyridin-3-yl)methyl](methyl)oxido-$\lambda^4$-sulphanylidenecyanamide (known from WO 2007/095229), sulphoxaflor (likewise known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911) and 1-{2,4-dimethyl-5-[(2,2,2-trifluoroethyl)sulphinyl]phenyl}-3-(trifluoromethyl)-1H-1,2,4-triazole (known from WO 1999/55668).

The compositions according to the invention preferably comprise
at least one insecticide selected from deltamethrin, beta-cyfluthrin, cyfluthrin, cypermethrin, alpha-cypermethrin, bendiocarb, bifenthrin, permethrin, pyrethrum, lambda-cyhalothrin, gamma-cyhalothrin, etofenprox, pyrethrum, especially natural pyrethrum, indoxacarb, carbaryl, fipronil, metaflumizone, azadirachtin, flubendiamide, chlorantraniliprole, boric acid, borax, imidacloprid, clothianidin, dinotefuran and acetamiprid, fenpyroximate, fipronil and tolfenpyrad, spinosad.

The compositions according to the invention more preferably comprise
at least one insecticide selected from deltamethrin, beta-cyfluthrin, cyfluthrin, lambda-cyhalothrin, bendiocarb, natural pyrethrum and fipronil.

Most preferably in accordance with the invention, deltamethrin is one of the insecticides present in the composition.

Preference is given to compositions according to the invention having a single active insecticidal ingredient, especially having deltamethrin.

The inert carriers used in accordance with the invention are standard inert carriers having a melting point between 50 and 160° C., preferably between 60 and 140° C. and more preferably between 70 and 120° C. under standard conditions. These are referred to in the description as wax.

Useful waxes preferably include plant waxes, for example cotton wax, carnauba wax, candelilla wax, japan wax, sugarcane wax; animal waxes, for example beeswax, wool wax, shellac wax; mineral waxes, for example ceresin, ozokerite, montan wax. In addition, it is possible in accordance with the invention to use chemically modified waxes, for example hydrogenated jojoba waxes, montan ester wax, and fully synthetic waxes such as polyalkylene waxes, polyethylene glycol waxes, amide waxes, Fischer-Tropsch paraffin waxes and fluorocarbon waxes.

Further suitable waxes in accordance with the invention are hydrogenated and non-hydrogenated fats, e.g. triglycerides, or fatty acids, for example stearin, coconut fat or hydrogenated oils, for example hydrogenated palm oil or hydrogenated castor oil.

The waxes may be used in accordance with the invention in macrocrystalline, microcrystalline or amorphous form.

Particular preference is given in accordance with the invention to using carnauba wax and montan wax as wax. Very particular preference is given to carnauba wax.

The insecticide-wax particles according to the invention preferably comprise no further components apart from wax and insecticide(s), as defined above. More particularly, they preferably do not comprise any pheromones, any carbohydrate polymers, any oil-absorbing substances (especially any starch, starch derivatives, cellulose, amorphous silicon dioxide, clay, talc), any inorganic carriers, any evaporation inhibitors, any fertilizers, or any mineral oil which is liquid under standard conditions.

For the performance of the above-described process steps (a) and (b), different variants are conceivable. For example, the wax can be melted in a tank. Thereafter, an active insecticidal ingredient is or active insecticidal ingredients are dispersed into the wax melts without adding water and without adding additives and auxiliaries. For this operation, it is possible to use standard mixing equipment which is known to be used for the production of agrochemical formulations. The mixture can, as described in WO2012/080188 A1, be processed further via spray solidification to give the insecticide-wax particles. Also conceivable is further processing via emulsifying solidification (by dispersion of the hotmelt in water or oil) or further processing of the melt with a fluidized bed drier (cooling of the hotmelt by means of a fluidized bed). For reasons of cost, however, it is particularly advantageous and preferable in accordance with the invention when the melt is cooled down as a block (with particularly preferred dimensions of 1000 mm×1000 mm×200 mm) in an appropriate vessel (preferably a metal vessel) and preferably beneath a ventilated fume hood at temperatures of preferably between −10° and 500 Celsius and preferably between 15° and 35° Celsius and then processed further via dry grinding. In this case, the cooled blocks are first comminuted mechanically to give lumps and then processed with the aid of comminuting machines for dry grinding, such as crushers, friction machines, dry grinding units, Frewitt sieve grinding units, ball mills, stirred ball mills, circulation mills, disc mills, annular chamber mills, double cone mills, three-roll mills, batch mills, more preferably with Frewitt sieve grinding units, to give active ingredient-wax particles having a median particle size d50 between 0.1 to 10 mm, preferably 0.5 to 5 mm and more preferably 0.8 to 2 mm. According to the invention, the term "dry grinding" encompasses any form of mechanically assisted and/or manual comminution of a composition which is dimensionally stable at room temperature.

In a further preferred embodiment of the above-described preparation process, the particles obtained in step (b) have a median particle size of 0.1 to 10 mm (preferably 0.5 to 5 mm and more preferably 0.8 to 2 mm) and are brought, in step (c), together with water and standard additives and auxiliaries, by grinding, preferably by wet grinding, to a median particle size of 5 to 40 µm. Alternatively, the grinding in step (c) is effected by means of an air-jet mill and the dispersion in water is effected after the grinding step. In step (c), however, preference is given in accordance with the invention to wet grinding.

In process step (c), the sequence in which the constituents (i.e. water, additive and auxiliaries and active ingredient-wax particles produced in process step (a) and (b)) are blended with one another is as desired. However, a thickener is typically added last. Preferably, wet grinding methods known for the production of agrochemical formulations and known mixing units are used.

WO2012/080188 A1 states that the solid components apart from the active ingredient-wax particles according to the invention are appropriately used in the finely ground state. Surprisingly, however, it has now been found that the solid components comprising the active ingredient-wax particles obtained from process step (b) (but preferably without the thickener) and water can be subjected to a wet grinding operation, optionally over several stages. This is surprising since waxes are very ductile substances and typically do not have the brittleness required for wet grinding. Wet grinding methods and equipment required for the purpose are sufficiently well known to those skilled in the art. For example, it is possible to use ball mills, rotor-stator mills or suitable stirrers (such as dissolver discs). Preference is given to using rotor-stator mills and/or ball mills.

The temperatures in process step (c) can be varied within a particular range in the course of production of the composition. Suitable temperatures are between 10° C. and 60° C., preferably between 15° C. and 40° C.

As well as the above-detailed wax-insecticide particles, the compositions according to the invention comprise one or more customary auxiliaries or additives from the groups of the dispersing aids, the separating agents (anti-caking agents), the antifreezes, the foam inhibitors, the preservatives, the antioxidants, the spreading agents, the dyes, the thickeners (optionally including thickening activator), one or more acids or bases (in an amount for controlled adjustment of the pH of the composition or for thickener activation). The term "customary auxiliaries or additives" is understood in the sense of the aforementioned definition throughout this application.

Useful thickeners are all substances that are typically usable for this purpose in agrochemical compositions and function as thickening agents. Preference is given to inorganic particles such as carbonates, silicates and oxides, and also organic substances such as urea-formaldehyde condensates. Examples additionally include kaolin, rutile, silicon dioxide, finely divided silica, silica gels, and natural and synthetic silicates, and also talc. Thickeners used may additionally be synthetic thickeners such as polyacrylate thickeners (e.g. Carbopol® and Pemulen® thickeners from Lubrizol, Cleveland, USA), biological thickeners (e.g. Kelzan® S, xanthan gum, or further hydrocolloids from CP Kelco, Atlanta, USA) and inorganic thickeners (e.g. sheet silicates such as kaolin, montmorillonite and laponite). Particularly suitable in accordance with the invention are biological thickeners, for example heteropolysaccharides, for example anionic heteropolysaccharides such as xanthan gum. Particular preference is given to xanthan gum (Kelzan® S).

The separating agents (anti-caking agents) used, which are intended to prevent lump formation and caking of composition constituents, are conventional separating agents. Preference is given in accordance with the invention to using fumed silica (amorphous fumed silica, e.g. Aerosil®, from Evonik Industries).

Suitable acids or bases for pH adjustment are standard organic and inorganic acids and bases. Preference is given to using, as base, weak inorganic bases such as aqueous ammonia and, as acids, weak organic acid, for example citric acid. These are added to the composition in suitable amounts in order to establish the desired pH. The pH (at RT) of the composition is typically between 3-7.

Useful foam inhibitors are all substances usable for this purpose in agrochemical compositions. Preference is given to silicone oils and magnesium stearate. Particularly suitable in the context of the invention is Rhodorsil® (from Bluestar Silicones), a polydimethylsiloxane which is supplied in aqueous emulsion.

According to the invention, it is optionally also possible to use dispersing aids. Useful for this purpose are, for example, customary emulsifiers, especially customary wax emulsifiers. Particular mention should be made here of wax emulsifier 4106® (from Clariant), a mixture of alkyl ethoxylates. This is a nonionic emulsifier which is used with preference in accordance with the invention.

Dispersing aids used may also be surfactants. Useful nonionic surfactants in addition to the aforementioned include all substances of this type which are typically usable in agrochemical compositions. Preference is given to polyethylene oxide-polypropylene oxide block copolymers, polyethylene glycol ethers of linear alcohols, reaction products of fatty acids with ethylene oxide and/or propylene oxide, and also polyvinyl alcohol, polyvinylpyrrolidone, copolymers of polyvinyl alcohol and polyvinylpyrrolidone, copolymers of polyvinylacetate and polyvinylpyrrolidone, and copolymers of (meth)acrylic acid and (meth)acrylic esters, and additionally alkyl ethoxylates and alkylaryl ethoxylates, which may optionally be phosphated and optionally be neutralized with bases, polyoxyamine derivatives and nonylphenol ethoxylates.

Suitable anionic surfactants include all substances of this type that can typically be used in agrochemical compositions. Preference is given to alkali metal salts and alkaline earth metal salts of alkylsulphonic acids or alkylarylsulphonic acids.

A further preferred group of anionic surfactants and/or dispersing assistants is that of salts of polystyrenesulphonic acids, salts of polyvinylsulphonic acids, salts of naphthalenesulphonic acid-formaldehyde condensation products, salts of condensation products of naphthalenesulphonic acid, phenolsulphonic acid and formaldehyde, and salts of lignosulphonic acid.

Preference is given to nonionic surfactants selected from the group of the polyethylene glycol ethers of linear alcohols, reaction products of fatty acids with ethylene oxide or propylene oxide.

Useful antifreezes include all substances of this type which are typically usable in agrochemical compositions. Preference is given to urea, glycerol or propylene glycol. A further preferred group of antifreezes is that of additives from the group of the polyglycerols or polyglycerol derivatives. According to the invention, particular preference is given to using 1,2-propylene glycol.

Useful preservatives include all substances which are typically usable for this purpose in agrochemical compositions of this type. Examples include Preventol® (mixture of 2 isothiazolones, from Lanxess AG) and Proxel® (1,2-benzisothiazol-3-one, from Arch Chemicals, Inc.).

Useful antioxidants are all substances typically usable for this purpose in agrochemical compositions. Preference is given to butylhydroxytoluene (2,6-di-t-butyl-4-methylphenol, BHT).

Useful spreading agents are all substances typically usable for this purpose in agrochemical compositions. Preference is given to polyether siloxanes or organomodified polysiloxanes.

Useful dyes are all substances typically usable for this purpose in agrochemical compositions. Examples include titanium dioxide, pigment black, zinc oxide and blue pigments, and also Permanent Red FGR.

The proportion of active ingredient in suspension concentrates according to the invention can be varied within a wide range. All % figures in this description are % by weight, unless stated otherwise.

In a preferred embodiment of the suspension concentrate according to the invention, the concentration of active ingredient, preferably of deltamethrin, in the wax based on one active ingredient-wax particle is between 20% and 30% by weight.

In suspension concentrates according to the invention, which are diluted with water prior to use, the amount of active ingredient is typically 0.5% to 5% by weight, preferably 0.5% to 2.5% by weight, for example about 1% by weight, based on the suspension concentrate.

According to the invention, the water content in suspension concentrates is about 65% to 90%, preferably 70% to 85%, based on the suspension concentrate.

According to the invention, the proportion of wax in the suspension concentrates is preferably about 2% to 13%, preferably about 3% to 11.5% and more preferably 4% to 10%, based on the suspension concentrate.

The auxiliaries and additives make up the remainder of the suspension concentrate.

In general, the suspension concentrates, for production of a ready-to-use formulation (i.e. the spray liquor), are diluted with water in a ratio of 1:50 to 1:500 according to the desired active ingredient concentration.

In the case of formulations diluted for use (i.e. the spray liquor), the active ingredient content is generally, according to the active ingredient, between 0.00025% and 1% by weight, preferably between 0.00125% and 0.5% by weight, more preferably between 0.0025% and 0.25% by weight, based on the ready-to-use overall composition.

In a further preferred embodiment of the invention, the concentration of active ingredient, based on the final concentration in the suspended aqueous formulation, is between 20 and 30 g/litre.

When used in their commercially available formulations and in the use forms prepared from these formulations, the compositions according to the invention may also be present in a mixture with synergists. Synergists are compounds which enhance the activity of the active ingredients present in the compositions according to the invention, with no need for the added synergist itself to be active.

Application is accomplished in a customary manner appropriate for the use forms.

The active ingredients usable in accordance with the invention, given good plant tolerance, favourable homeotherm toxicity and good environmental compatibility, are suitable for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They are active against normally sensitive and resistant species and also against all or some stages of development.

The compositions according to the invention can preferably be used to kill harmful or annoying arthropods, especially arachnids and insects such as sucking or biting insects. The particularly preferred arachnids include scorpions, spiders, mites and ticks. The particularly preferred sucking insects include essentially mosquitoes, moth flies, gnats, blackflies, biting houseflies, tsetse flies, horseflies, common houseflies, flesh flies, myiasis-causing flies, bugs and sandflies. The particularly preferred biting insects include essentially cockroaches, beetles, termites, ants, wasps and moth larvae. Most preferably, the materials according to the invention are used against spiders, mosquitoes, flies, bugs, cockroaches, ants and beetles. Most preferably, the invention is used against cockroaches and/or ants.

If the compositions according to the invention are in non-ready-to-use form (for example as an aqueous suspension concentrate), they are first diluted in water for their use as intended. Dilution is effected to such an extent that the active ingredient content assures adequate insecticidal action at the intended application rate. The dilution gives rise to compositions which correspond to the above-specified ready-to-use compositions.

The diluted spray solution (also referred to in the application as spray liquor) can be sprayed in any customary manner, for example by means of manual or electrical sprayers.

Preferably, the compositions according to the invention are applied to a surface in such a dilution and application rate that the application of the active ingredient-wax particles per unit area (based on solids) is from 0.25 mg/m$^2$ to 5000 mg/m$^2$, preferably from 0.25 mg/m$^2$ to 2500 mg/m$^2$, more preferably from 0.5 mg/m$^2$ to 1250 mg/m$^2$ and especially preferably from 5 mg/m$^2$ to 1000 mg/m$^2$.

The compositions according to the invention can be applied to any desired surface within buildings or outdoors, for example carpets, concrete, cement, wall or floor tiles, concrete, building stone, wood (treated and untreated), ceramic (glazed and unglazed), straw or thatch, brick (plain, whitewashed, painted), clay minerals (e.g. terracotta), chalk-containing, lime-containing, gypsum-containing, cement-containing and loam-containing surfaces, or else to plants such as grass.

The examples which follow serve to illustrate the invention and should in no way be interpreted in a restrictive way.

USE EXAMPLES

Example 1: Production of the Composition According to the Invention

Deltamethrin-containing wax particles are produced by melting a mixture of 80 kg of carnauba wax T4 and 20 kg of deltamethrin TC in a stirred tank at 130° C. and then homogenizing the mixture by stirring until melting is complete.

The mixture is cooled down to 110° C. in the tank and then poured into several flat metal moulds. The melt solidifies in the metal moulds at room temperature. The solidified mass is removed from the mould by mechanical means and ground to a small particle size of about 1-3 ml in several dry grinding steps by means of crushers and friction.

To an initial charge of 129 g of demineralized water in a tank are successively added, while stirring, 120 g of wax emulsifier 4106 (alkoxy ethoxylate mixture CAS No. [68920-66-1], Clariant International AG, Muttenz, Switzerland) MX 25% (30 g of wax emulsifier 4106 in demineralized water), 5 g of Aerosil 200 (synthetic amorphous silicon dioxide, Evonik Degussa GmbH, DE), 0.4 g of Acticide CT (55965-84-9, mixture of: 5-chloro-2-methyl-2H-isothiazol-3-one [EC No 247-500-71<2.5%, and 2-rnethyl-2H-isothiazol-3-one, Thor GmbH, Germany), 2 g of citric acid (anhydrous), 1 g of Rhodorsil 426 R (20-30% aqueous emulsion of polydimethylsiloxane, Bluestar Silicones, FR), and the mixture is homogenized to give a preliminary solution.

Subsequently, 122.55 g of deltamethrin-containing wax particles (24.51 g of deltamethrin in carnauba wax T4 Ter Hell, grated to 3 mm) are added to the preliminary solution with homogenization by means of a Silverson homogenizer (L4RT type) at 5000 rpm, and homogenized at 7700 rpm for a further 5 min. This is followed by preliminary comminution in a Fryma mill (MZ 100=2850 rpm, closed, or friction gap 0.3 mm) and then 2 grinding runs in a 1.4 l Bachofen wet mill with 1.25 to 2 mm zirconium beads, mill loading 80% and circumferential speed 10 m/s. The rate of metered addition is between 8 to 17 kg/h. Finally, 180 g of demineralized water, 60 g of 1,2-propylene glycol (monopropylene glycol, CAS No.: 57-55-6, Solvadis, Brenntag, BASF, BP, Quimidroga, CVH Chemie-Vertrieb, Petrochem Carless, OXYDE CHEMICALS, Inc., Polioles, Shell, ALVEG), 380 g of Kelzan S (xanthan gum, CAS 011138-66-2, F. B. Silbermann GmbH & Co KG, DE) and MX 2% (7.6 g of Kelzan S, 0.38 g of 24-30% ammonia solution, 0.76 g of Acticide CT in 371.26 g of demineralized water) are added and homogenized by means of a toothed-disc stirrer for a further 30 to 60 min.

The FIGURE shows a microscope image (ESEM Quanta 400 scanning electron microscope from FEI Company Deutschland GmbH) of the surface of active ingredient-wax particles produced according to Example 1. The active ingredient crystals on the surface of the particles are clearly apparent.

Example 2: Biological Efficacy of the Composition According to the Invention Compared to Those According to WO2012/080188

Suspension concentrates produced according to Example 1 and according to the teaching of WO2012/080188 (see use examples a) and b)) were diluted and sprayed onto various surfaces (tile, wood, concrete) in a concentration of 6.25 mg of active ingredient/m$^2$. After the ageing time specified in Table 1, the mortality and knockdown of *Blattella germanica* was determined in a bioassay. Both insecticidal compositions led to similarly good results.

| Test composition | Surface area | Ageing time | mg of active ingredient/ m$^2$ | Knockdown after 1 hour in % | Knockdown after 2 hours in % | Mortality after 24 h in % |
|---|---|---|---|---|---|---|
| Inventive suspension concentrate | Tile | 1 day | 6.25 | 93 | 100 | 100 |
| | | 2 weeks | 6.25 | 100 | 100 | 100 |
| | | 6 weeks | 6.25 | 100 | 100 | 100 |
| | | 13 weeks | 6.25 | 100 | 100 | 100 |
| Suspension concentrate according to WO2012/080188 | Tile | 1 day | 6.25 | 100 | 100 | 100 |
| | | 2 weeks | 6.25 | 100 | 100 | 100 |
| | | 6 weeks | 6.25 | 100 | 100 | 100 |
| | | 13 weeks | 6.25 | 100 | 100 | 100 |
| Inventive suspension concentrate | Wood | 1 day | 6.25 | 93 | 100 | 100 |
| | | 2 weeks | 6.25 | 100 | 100 | 100 |
| | | 6 weeks | 6.25 | 100 | 100 | 100 |
| | | 13 weeks | 6.25 | 100 | 100 | 100 |
| Suspension concentrate according to WO2012/080188 | Wood | 1 day | 6.25 | 93 | 100 | 100 |
| | | 2 weeks | 6.25 | 100 | 100 | 100 |
| | | 6 weeks | 6.25 | 100 | 100 | 100 |
| | | 13 weeks | 6.25 | 93 | 100 | 100 |
| Inventive suspension concentrate | Concrete | 1 day | 6.25 | 93 | 100 | 100 |
| | | 2 weeks | 6.25 | 100 | 100 | 100 |
| | | 6 weeks | 6.25 | 93 | 93 | 100 |
| | | 13 weeks | 6.25 | 87 | 100 | 100 |
| Suspension concentrate according to WO2012/080188 | Concrete | 1 day | 6.25 | 100 | 100 | 100 |
| | | 2 weeks | 6.25 | 100 | 100 | 100 |
| | | 6 weeks | 6.25 | 100 | 100 | 100 |
| | | 13 weeks | 6.25 | 100 | 100 | 100 |

The invention claimed is:

1. A process for producing an insecticidal composition comprising (i) at least one active insecticidal ingredient, (ii) wax having a melting point of 50 to 160° C., (iii) water, and (iv) one or more additives and/or auxiliaries, wherein the insecticidal active ingredient(s) is/are dispersed in the wax and the insecticidal-containing wax is present in the composition in the form of particles having a mean particle size of 5 to 40 μm, and crystals of the active ingredient(s) are present at the surface of the particles, comprising (a) melting the wax and dispersing the active insecticidal ingredient(s) in the melt without adding water and without adding additives and auxiliaries, (b) cooling the mixture in a vessel as a block and comminuting the block by subsequent dry grinding, and (c) dispersing and wet grinding the resultant particles in water with addition of one or more additives and auxiliaries.

2. The process for producing an insecticidal composition according to claim 1, wherein the active insecticidal ingredient is selected from the group consisting of deltamethrin, beta-cyfluthrin, cyfluthrin, cypermethrin, alpha-cypermethrin, bendiocarb, bifenthrin, permethrin, pyrethrum, lambda-cyhalothrin, gamma-cyhalothrin, etofenprox, indoxacarb, carbaryl, fipronil, metaflumizone, azadirachtin, flubendiamide, chloranthraniliprole, boric acid, borax, imidacloprid, clothianidin, dinotefuran, acetamiprid, fenpyroximate, tolfenpyrad, and spinosad.

3. The process for producing an insecticidal composition according to claim 1, wherein the wax used is a carnauba wax or montan wax.

4. The process for producing an insecticidal composition according to claim 1, wherein, in (b), the mixture is cooled as a block in a vessel at temperatures between −10° and 50° Celsius.

5. The process for producing an insecticidal composition according to claim 1, wherein particles obtained in (b) have a median particle size of 0.1 to 10 mm.

6. The process for producing an insecticidal composition according to claim 1, wherein the wet grinding is conducted by means of at least one rotor-stator mill and/or at least one ball mill.

7. The process for producing an insecticidal composition according to claim 1, wherein the active insecticidal ingredient is deltamethrin.

8. The process for producing an insecticidal composition according to claim 7, wherein the wax is carnauba wax.

9. The process for producing an insecticidal composition according to claim 1, wherein the insecticidal composition has a single active ingredient.

10. The process for producing an insecticidal composition according to claim 9, wherein the single active ingredient is deltamethrin.

11. The process for producing an insecticidal composition according to claim 1, wherein the wet grinding takes places in the absence of a thickener.

12. The process for producing an insecticidal composition according to claim 1, wherein the insecticidal composition is a suspension concentrate.

13. The process for producing an insecticidal composition according to claim 12, wherein the suspension concentrate comprises active ingredient-wax particles containing 20 to 30% by weight of deltamethrin.

14. The process for producing an insecticidal composition according to claim 13, wherein the suspension concentrate comprises 2 to 13% by weight of wax.

15. The process for producing an insecticidal composition according to claim 12, wherein the suspension concentrate is further diluted with water in a ratio of 1:50 to 1:500 to produce a ready-to-use formulation.

\* \* \* \* \*